(12) United States Patent
Nielsen et al.

(10) Patent No.: US 8,821,780 B2
(45) Date of Patent: Sep. 2, 2014

(54) METHOD AND MACHINE FOR PRODUCING A HOLLOW PRODUCT

(75) Inventors: Henrik Lindenskov Nielsen, Smoerum (DK); Per-Erik Magnusson, Hörby (SE)

(73) Assignee: Nolato Meditech AB, Hoerby (SE)

( * ) Notice: Subject to any disclaimer, the term of this patent is extended or adjusted under 35 U.S.C. 154(b) by 819 days.

(21) Appl. No.: 12/089,031

(22) PCT Filed: Oct. 3, 2006

(86) PCT No.: PCT/SE2006/001123
§ 371 (c)(1),
(2), (4) Date: Nov. 5, 2008

(87) PCT Pub. No.: WO2007/040441
PCT Pub. Date: Apr. 12, 2007

(65) Prior Publication Data
US 2009/0118688 A1    May 7, 2009

(30) Foreign Application Priority Data
Oct. 3, 2005  (SE) ...................... 0502188

(51) Int. Cl.
| | |
|---|---|
| *B29C 45/73* | (2006.01) |
| *B29C 45/78* | (2006.01) |
| *A61F 5/453* | (2006.01) |
| *B29C 45/42* | (2006.01) |
| *B29C 45/27* | (2006.01) |
| *B29C 45/26* | (2006.01) |
| *B29L 31/00* | (2006.01) |
| *B29K 21/00* | (2006.01) |
| *B29C 45/34* | (2006.01) |
| *B29K 83/00* | (2006.01) |

(52) U.S. Cl.
CPC ......... *B29C 45/2756* (2013.01); *B29C 45/2669* (2013.01); *B29L 2031/753* (2013.01); *A61F 5/453* (2013.01); *B29C 45/4225* (2013.01); *B29K 2021/006* (2013.01); *B29C 45/34* (2013.01); *B29C 45/2711* (2013.01); *B29K 2083/005* (2013.01)
USPC ................. 264/328.16; 264/328.14; 264/40.5

(58) Field of Classification Search
USPC ....................................... 264/328.2
See application file for complete search history.

(56) References Cited

U.S. PATENT DOCUMENTS

| | | |
|---|---|---|
| 3,608,552 A | 9/1971 | Broerman |
| 3,835,857 A | 9/1974 | Rogers, III et al. |

(Continued)

FOREIGN PATENT DOCUMENTS

| | | |
|---|---|---|
| DE | 1026044 | 3/1958 |
| EP | 162037 A2 | 11/1985 |

(Continued)

OTHER PUBLICATIONS

G. Steinbichler, "Spritzgiessen Von Fluessigsiliconkautschuk", Kunststoffe, Carl Hanser Verlag, Muenchen, Germany, XP001176509, vol. 77, No. 10, pp. 931-933 (Oct. 1, 1997).

(Continued)

*Primary Examiner* — Monica Huson
(74) *Attorney, Agent, or Firm* — Martin & Ferraro, LLP

(57) ABSTRACT

A method and injection machine for producing a hollow product, such as a urisheath, use of the method for producing a urisheath as well as the urisheath. The machine comprises an annular cavity for receiving a silicone material. The material is injected in a cold state via a coldrun nozzle (20) and cured by heat in the cavity. The cavity has a narrow cross-sectional area over a substantial portion of the cavity and the cavity is connected to a venting area (13). The cavity has an annular enlarged portion (18) at the proximal portion of the cavity, arranged adjacent said inlet (24) and a groove (14) at the distal portion of the cavity. The narrow cross-sectional area has a decreasing radial dimension towards the distal portion of the cavity. The surface of the cavity is grit blasted.

18 Claims, 5 Drawing Sheets

(56) References Cited

U.S. PATENT DOCUMENTS

| | | |
|---|---|---|
| 3,901,965 A | 8/1975 | Honeyman, III |
| 4,149,695 A | 4/1979 | Quick et al. |
| 4,475,910 A | 10/1984 | Conway |
| 4,581,026 A | 4/1986 | Schneider |
| 4,594,277 A | 6/1986 | Galli et al. |
| 4,594,761 A * | 6/1986 | Murphy et al. ............ 29/889.71 |
| 4,732,724 A | 3/1988 | Sterner |
| 4,734,241 A | 3/1988 | Gerow |
| 4,865,595 A | 9/1989 | Heyden |
| 4,872,463 A | 10/1989 | Nishizono |
| 4,934,382 A | 6/1990 | Barone |
| 4,972,850 A | 11/1990 | Broad |
| 5,176,666 A | 1/1993 | Conway et al. |
| 5,334,175 A | 8/1994 | Conway et al. |
| 5,376,085 A | 12/1994 | Conway et al. |
| 5,459,879 A | 10/1995 | Fuchs |
| 5,531,725 A | 7/1996 | Steer |
| 5,554,141 A | 9/1996 | Wendler |
| 5,685,870 A | 11/1997 | Tanghoj |
| 5,713,880 A | 2/1998 | Anderson |
| 5,779,964 A | 7/1998 | Welch et al. |
| 6,250,303 B1 | 6/2001 | Delaney |
| 6,376,432 B1 | 4/2002 | Leslie et al. |
| 6,726,363 B1 | 4/2004 | Marbler et al. |
| 6,732,736 B2 | 5/2004 | Sanchez |
| 6,805,690 B2 | 10/2004 | Ogden et al. |
| 2003/0212375 A1 | 11/2003 | Ogden et al. |
| 2005/0101923 A1 | 5/2005 | Elson |
| 2008/0215021 A1 | 9/2008 | Cisko Jr. et al. |
| 2008/0257360 A1 | 10/2008 | Nielsen |
| 2009/0018530 A1 | 1/2009 | Nielsen et al. |
| 2011/0118685 A1 | 5/2011 | Nielsen et al. |
| 2011/0257615 A1 | 10/2011 | Nielsen et al. |

FOREIGN PATENT DOCUMENTS

| | | |
|---|---|---|
| EP | 710535 A1 | 5/1996 |
| EP | 979718 A1 | 2/2000 |
| EP | 1 063 007 A1 | 12/2000 |
| FR | 2 649 315 | 1/1991 |
| FR | 2 734 754 | 12/1996 |
| FR | 2771923 | 6/1999 |
| GB | 2 286 339 | 8/1995 |
| GB | 2 357 725 | 7/2001 |
| JP | 57-209051 A | 12/1982 |
| JP | 58-001445 A | 1/1983 |
| JP | 58001529 A | 1/1983 |
| JP | 60-229716 A | 11/1985 |
| JP | 61-277419 A | 12/1986 |
| JP | 62-070012 A | 3/1987 |
| JP | 01 110116 A | 4/1989 |
| JP | 3-33617 U | 4/1991 |
| JP | 4-19117 | 1/1992 |
| JP | 5-506381 A | 9/1993 |
| JP | H06-501412 A | 2/1994 |
| JP | 7-002019 U | 1/1995 |
| JP | 07-9317 | 2/1995 |
| JP | 7-299090 | 11/1995 |
| JP | 08-252277 | 10/1996 |
| JP | 8-336842 A | 12/1996 |
| JP | 10183162 A | 7/1998 |
| JP | 10-510452 | 10/1998 |
| JP | 10-291235 A | 11/1998 |
| JP | 2000-232988 | 8/2000 |
| JP | 2002-102110 A | 4/2002 |
| JP | 2003-211500 A | 7/2003 |
| JP | 2008-511360 A | 4/2008 |
| JP | 2008-543423 A | 12/2008 |
| WO | WO-91/17728 A1 | 11/1991 |
| WO | WO 92/08426 A1 | 5/1992 |
| WO | WO 93/00054 A1 | 1/1993 |
| WO | WO 93/03697 A1 | 3/1993 |
| WO | WO 97/40790 | 4/1996 |
| WO | WO-98/22275 A1 | 5/1998 |
| WO | WO 02/053070 A1 | 7/2002 |
| WO | WO 03/005940 | 1/2003 |
| WO | WO-2004/004796 A1 | 1/2004 |
| WO | WO-2006/024637 | 3/2006 |
| WO | WO 2007/099129 | 9/2007 |

OTHER PUBLICATIONS

English Translation of Japanese Office Action dated Jan. 5, 2012 for JP Application No. 2008-556777.

International Search Report, PCT/EP2007/051916, completed Sep. 13, 2007, mailed Oct. 10, 2007, 3 pages.

* cited by examiner

METHOD AND MACHINE FOR PRODUCING A HOLLOW PRODUCT

FIELD OF INVENTION

The present invention relates to a method of producing a hollow, thin-walled product, such as a urisheath, by an injection molding process and an injection molding machine therefore. The invention also relates to the use of the injection molding machine for making a urisheath and a urisheath produced by the method.

BACKGROUND OF INVENTION

A urisheath is a product used in urinary catheter devices for aiding in male urinary incontinence and similar uses. The urisheath comprises a cylindrical sleeve enclosing the shaft of the penis and a tip portion to which a hose may be connected ending in a urine collection bag.

A urisheath is traditionally made by dipping a mandrel with a corresponding design into a latex solution. The dipping process may be repeated several times and the latex is cured between the immersions.

WO 91/17728 discloses a method for manufacturing a urisheath by thermoplastic processing of a thermoplastic material. The tip portion is produced by injection molding in a tool whereas the thin-walled cylindrical portion is produced integrally with the tip portion by a controlled extrusion and blow-molding.

WO 2004/004796 discloses a method for producing a urisheath in a thermoplastic process for providing a urisheath, which is substantially clear to allow inspection of an area of the skin beneath the urisheath with the urisheath material in contact with the skin. The tip portion may be produced by injection molding and the cylindrical portion by extrusion, extrusion blow molding, injection blow molding or cold rolling. The tip portion may form an integral part with the cylindrical portion or may be produced as a separate unit, which is subsequently connected with the cylindrical portion. It is also possible to produce the urisheath entirely by extrusion blow-molding.

It is noted that urisheaths made of latex are no longer permitted or suitable in many countries because of interactions with the skin. A urisheath made of a thermoplastic material is feasible. However, the thermoplastic material requires addition of plasticizers, which may involve problems in certain cases. A plasticizer can cause migration problems, which eventually can cause biological safety issues, and which also can cause deterioration of the performance of the skin adhesive on the urisheaths. A plasticizer can in certain cases also cause environmental problems. Urisheaths made of silicone plastic materials are known in the art. However, such silicone urisheaths are normally made by dipping a mandrel in a suitable silicone solution, one time or several times as mentioned above in connection with latex urisheaths. This process is time-consuming. Moreover, it is difficult to control the wall thickness in such a production method.

Injection molding of silicone materials is previously known from e.g. EP 162 037. This patent discloses a method of producing a silicone matt or silicone domes by injection molding of a silicone material into a cavity having a corresponding shape. The material may be a two-component silicone material being injected at a low temperature. The cavity and the form portions may be heated to a high temperature for rapid curing of the silicone material.

In such an injection-molding machine it may be difficult to remove the air when the cavity is filled with material. This problem is addressed in EP 979 718, which discloses suction ports for removing the air.

SUMMARY OF INVENTION

An object of the present invention is to provide a method and a machine for producing a silicone urisheath or similar product by injection molding.

By using an injection-molding machine, the wall thickness of the product may be controlled very precisely by the design of the cavity of the injection-molding machine. Thus, a thin-walled product of high quality can be produced.

In an aspect of the invention, there is provided a method of producing a hollow product, such as a urisheath, in an injection molding machine, including a mold comprising an annular cavity defined by a core and at least one side portion, where said cavity has a narrow cross-sectional area over a substantial portion of said cavity and said cavity is connected to a venting area; the method comprising: injecting a silicone material into an inlet of said cavity; curing by heating said injected material in said cavity; opening said mold by moving said at least one side portion to expose said core with the cured material forming said product; removing said product from said core by grasping one end adjacent said inlet and pulling the product from the core, wherein said cavity has an annular enlarged portion at the proximal portion of the cavity, arranged adjacent said inlet.

In another aspect of the invention, there is provided a method of producing a hollow product, such as a urisheath, in an injection molding machine, including a mold comprising an annular cavity defined by a core and at least one side portion, where said cavity has a narrow cross-sectional area over a substantial portion of said cavity and said cavity is connected to a venting area; the method comprising: injecting a silicone material into an inlet of said cavity; curing by heating said injected material in said cavity; opening said mold by moving said at least one side portion to expose said core with the cured material forming said product; removing said product from said core by grasping one end adjacent said inlet and pulling the product from the core, wherein said cavity comprises a groove at the distal portion of the cavity.

In a further aspect of the invention, there is provided a method of producing a hollow product, such as a urisheath, in an injection molding machine, including a mold comprising an annular cavity defined by a core and at least one side portion, where said cavity has a narrow cross-sectional area over a substantial portion of said cavity and said cavity is connected to a venting area; the method comprising: injecting a silicone material into an inlet of said cavity; curing by heating said injected material in said cavity; opening said mold by moving said at least one side portion to expose said core with the cured material forming said product; removing said product from said core by grasping one end adjacent said inlet and pulling the product from the core, wherein the narrow cross-sectional area has a decreasing radial dimension towards the distal portion of the cavity.

In a still further aspect of the invention, there is provided a method of producing a hollow product, such as a urisheath, in an injection molding machine, including a mold comprising an annular cavity defined by a core and at least one side portion, where said cavity has a narrow cross-sectional area over a substantial portion of said cavity and said cavity is connected to a venting area; the method comprising: injecting a silicone material into an inlet of said cavity; curing by heating said injected material in said cavity; opening said mold by moving said at least one side portion to expose said core with the cured material forming said product; removing said product from said core by grasping one end adjacent said inlet and pulling the product from the core, wherein the cavity is blasted.

The silicone material may be injected into said cavity by a coldrun nozzle in a cold state. The material may be injected into said cavity until material is received in said venting area. The material may be a liquid silicone elastomer material or a solid silicone material.

In yet another aspect of the invention, there is provided an injection molding machine for manufacturing a product, such as a urisheath, comprising: an annular cavity defined by a core and at least one side portion; a nozzle for feeding a silicone material into an inlet of said annular cavity; a heating means for heating said core and optionally said at least one side portion; opening means for moving said at least one side portion to expose said core; whereby said cavity has a narrow cross-sectional area over a distal portion of the cavity and the cavity is connected to a venting area, wherein said cavity has an annular enlarged portion at an proximal portion. Said inlet may be arranged at the top of a proximal portion of said cavity and an annular enlarged portion may be arranged at said inlet for forming a protruding push rim in the product to be formed. The enlarged portion may protrude outwards in the radial direction.

In yet a further aspect of the invention, there is provided an injection molding machine for manufacturing a product, such as a urisheath, comprising: an annular cavity defined by a core and at least one side portion; a nozzle for feeding a silicone material into an inlet of said annular cavity; a heating means for heating said core and optionally said at least one side portion; opening means for moving said at least one side portion to expose said core; whereby said cavity has a narrow cross-sectional area over a distal portion of the cavity and the cavity is connected to a venting area, wherein a groove is positioned adjacent said venting area for forming a roll rib in the product to be formed. Said groove may be arranged at the end portion of said distal portion of said cavity. Said groove may extend outwards in a radial direction.

In yet still another aspect of the invention, there is provided an injection molding machine for manufacturing a product, such as a urisheath, comprising: an annular cavity defined by a core and at least one side portion; a nozzle for feeding a silicone material into an inlet of said annular cavity; a heating means for heating said core and optionally said at least one side portion; opening means for moving said at least one side portion to expose said core; whereby said cavity has a narrow cross-sectional area over a distal portion of the cavity and the cavity is connected to a venting area, wherein said cross-sectional area has a decreasing radial dimension towards the distal end of the cavity.

Said venting area may comprise an overflow area and at least one venting channel adjacent an end portion of said distal portion for receiving surplus material injected in said cavity. Said nozzle may be a coldrun nozzle for injecting said material at a temperature of between 5° C. and 50° C., specifically between 15° C. and 40° C., more specifically between 20° C. and 30° C., still more specifically about 25° C. Said heating means may be arranged for heating said core and optionally said at least one side portion to a temperature of between 80° C. and 200° C., specifically between 100° C. and 160° C., more specifically between 110° C. and 150° C., still more specifically between 135° C. and 145° C.

In a further embodiment, the machine may further comprise removal means for removing said product from said core, wherein said removal means may comprise a sensor device for sensing that the entire product has been removed from the core.

In a yet further aspect of the invention, there is provided a use of an injection-molding machine as mentioned above, for making a urisheath from a silicone material.

In a yet still further aspect of the invention, there is provided a urisheath produced by a method as described above. The urisheath may be provided with a push rim and a roll rib.

BRIEF DESCRIPTION OF DRAWINGS

Further objects, features and advantages of the invention will appear from the description of an embodiment of the invention with reference to the accompanying drawings, in which.

DETAILED DESCRIPTION OF EMBODIMENTS

Figure 1:
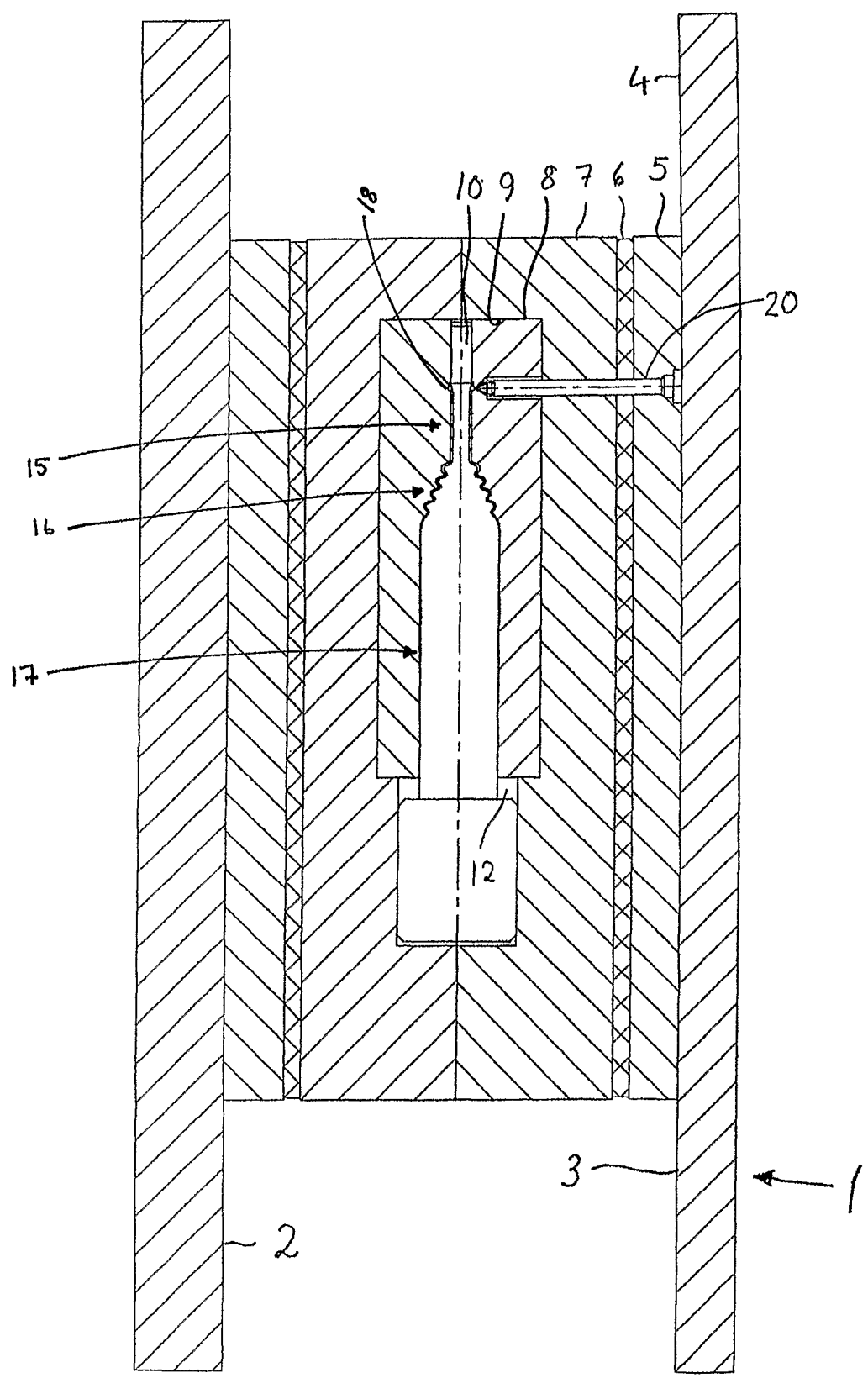
FIG. 1 is a cross-sectional view of an injection-molding tool for producing a urisheath according to the invention, shown in a closed position.

FIG. 1 discloses a cross-sectional view of an injection-molding tool for manufacturing a urisheath.

The injection-molding tool 1 comprises a left, movable form section 2 and a right, fixed form section 3. It is mentioned that left and right and other directions are only in relation to FIG. 1, while the injection molding tool may be arranged in any desired direction, vertically as shown in FIG. 1 or 90° or 180° in relation to the position shown in FIG. 1. The injection-molding tool may alternatively comprise one or several form sections.

Each form section 2, 3 comprise one or several support plates 4, 5 and a heat-insulating plate 6. The support plates 4, 5 and the insulating plate 6 together support a form plate 7. Form plate 7 comprises a recess 8 in which an insertion plate 9 is arranged. The insertion plate 9 is provided with recesses or shapes that form the outer shape of the product to be formed, i.e. the urisheath, or at least a part of the outer shape thereof.

Form section 2 and 3 are designed in a corresponding way, which is not described in detail here other than when there are differences between the form sections 2 and 3.

A core 10 is arranged and shaped for defining the inner dimensions of the urisheath.

Form plates 7 of form sections 2, 3 are heated by electrical heaters (not shown), arranged in the form plates 7. Moreover, core 10 is heated by an electrical heater (not shown) inserted in the center of the core. It is noted that other types of heaters may be used, e.g. hot water or oil under pressure circulating in a duct system in the form plates and the core.

An injection nozzle 20 is arranged in the fixed form section 3 for injection of material into a cavity formed between core 10 and the form plates 9 of form sections 2 and 3. The nozzle is arranged at one end of the cavity, the proximal end of the proximal portion 15 of the cavity. The injection nozzle may be designed as shown in EP 710 535, the contents of which is incorporated herein by reference. The injection nozzle is fixed in the cold support plates 5, 4 of the form section 3 and extends through the insulating plate 6 into the hot region of form plate 7 of the form section 3.

Figure 2:
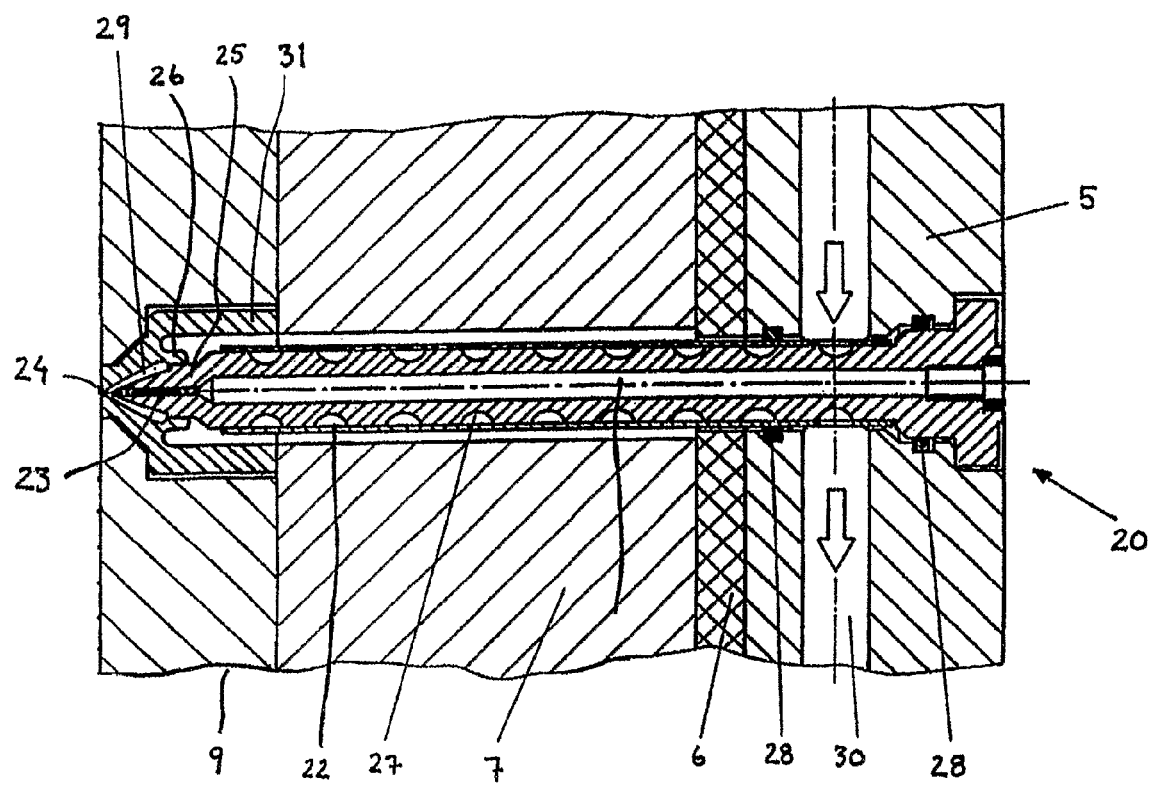
FIG. 2 is an enlargement of the injection area.

The injection nozzle 20 comprises a central injection channel 21 having a diameter of e.g. 2 mm as shown in FIG. 2. Exterior of the injection channel there is arranged a cooling jacket 22 enclosing several cooling channels 27 for a cooling medium such as water. Thus, the injection channel is maintained at a low temperature over its entire length. The injection channel ends in an injection channel portion 23 with a reduced diameter. The injection channel with reduced diameter ends slightly before an injection opening 24 to a cavity. An end portion 25 of the injection nozzle is supported by side walls 26 and forms a small cavity 29 which is filled by the injection material, which thereby forms a heat insulation for maintaining the reduced diameter channel portion 23 at a low temperature. Thus, the injection material can be fed to the injection cavity at a low temperature of e.g. about 25° C. Cold water is introduced in cooling channels 27 via a supply channel 30. The nozzle 20 is sealed by several O-ring sealings 28.

The side walls 26 supporting the end portion 25 of the injection nozzle may be arranged in an insert 31 which is replaceable, so that injection nozzles having different diameters and shapes may be used in the same form section by exchanging the insert 31 and the injection nozzle 20.

Figure 5:
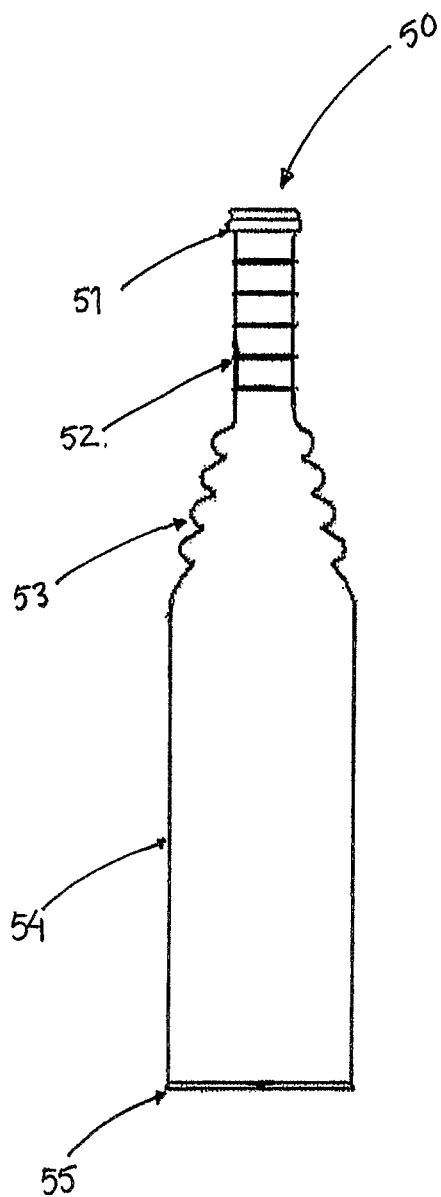
FIG. 5 is a side view of a product produced by machine and method according to the invention.

The proximal portion 15 of the cavity is designed to form the tip portion 52 of the urisheath, shown in FIG. 5, having a relatively large wall thickness. The distal portion 17 of the cavity is designed to form the cylindrical portion 54 of the urisheath. The cavity has a narrow cross-sectional area, resulting in a cylindrical portion having small wall thickness. The thickness of the cylindrical portion may be constant. However, if the cross-sectional area of the cavity has a decreasing radial dimension, resulting in a cylindrical portion having a reduced thickness towards the distal end of the cylindrical portion, some advantages are added to the product. A very thin urisheath will provide increased wearing comfort, as well as it may provide a more breathable product and thereby increasing the skin friendliness. A larger thickness in the proximal end of the cylindrical portion prevents the urisheath from ballooning when in use, and thereby prevents a radial force on the adhesive, which eventually can loosen the adhesive from the skin and be the cause for a leakage.

The cylindrical portion may have a constant radius or may have certain conicity.

FIG. 1 shows the injection-molding tool in a closed position ready for injection of material in the cavity. This takes place by feeding material through the injection nozzle 20 to the cavity. The material is injected into the proximal portion 15 as seen in FIG. 1. The proximal portion corresponds to the tip portion 52 of the ready-made urisheath. The tip portion has the largest wall thickness. Moreover, the proximal end of the proximal portion 15 has an enlarged portion 18, in which the injected material can be distributed circumferentially around the entire periphery of the cavity. This ensures that the cavity is filled with material in a uniform manner.

The enlarged portion 18 forms a protruding push rim 51 on the urisheath, shown in FIG. 5. This protruding push rim protrudes outwards in a radial direction from the tip portion 52. The protruding push rim is usable when removing the urisheath from the form. Furthermore, the protruding push rim may provide frictional engagement for handling of the product during use. This is useful when connecting the urisheath to a urine bag.

The push rim may, in an alternative embodiment, extend inwards, completely or partially, i.e. extend both inwards and outwards in the radial direction.

The enlarged portion 18 in the cavity forms an area for receiving the material injected into the cavity and distribute the material around the periphery of the enlarged portion before the material proceeds downward into the rest of the cavity. The material then proceeds downward essentially parallel at all sides of the cavity. Thus, the air in the cavity is expelled more easily and uniformly, which means that the risk of entrapping air inside the cavity is reduced or completely eliminated.

Figure 3:
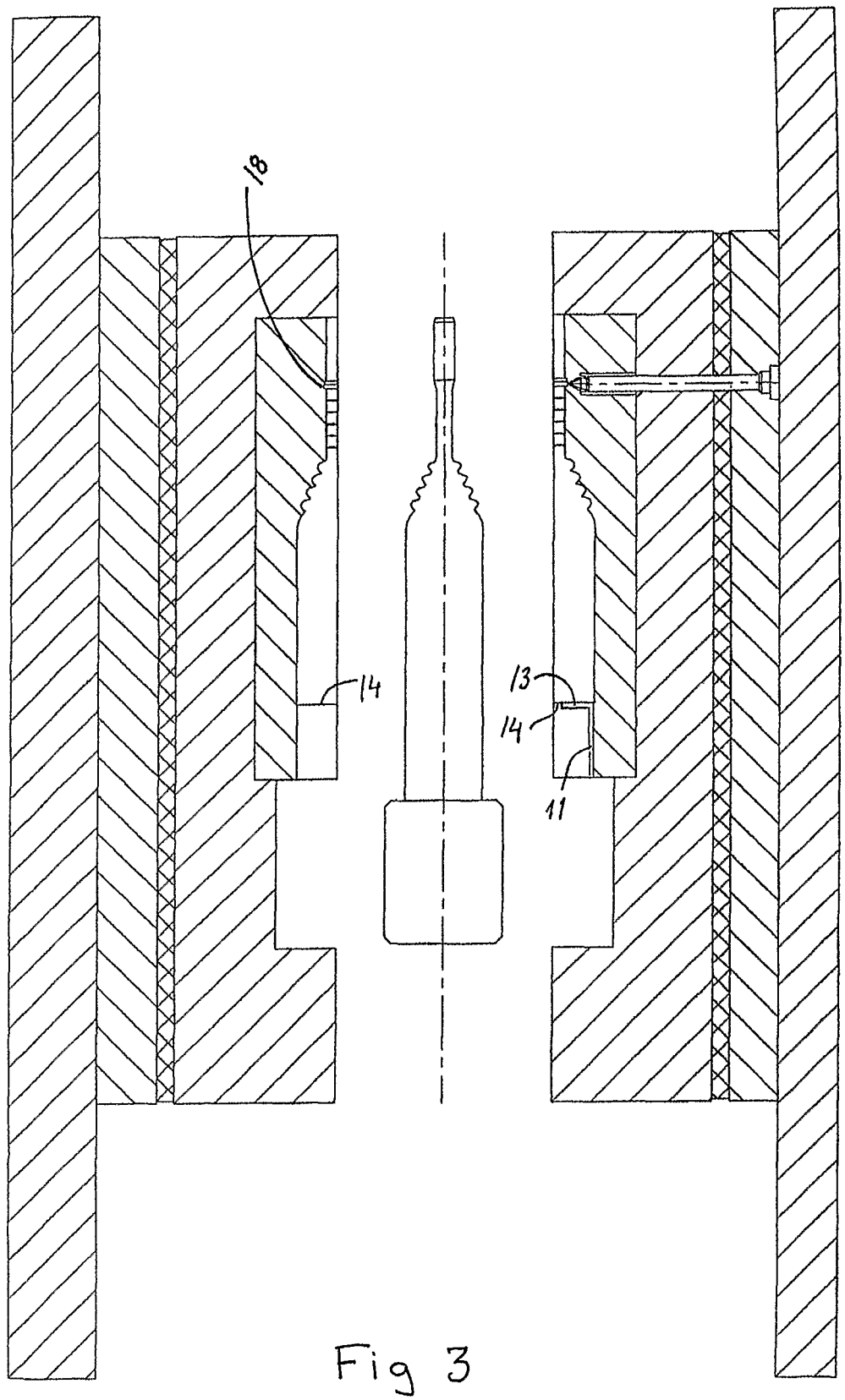
FIG. 3 is a cross-sectional view similar to FIG. 1, wherein the injection-molding tool is shown in an opened position.

The material proceeds downward inside the cavity and finally reaches the distal end of the distal portion 17 of the cavity. An overflow area 13 is arranged at the distal end of the distal portion of the cavity. When the material reaches the overflow area, some material proceeds out in said area. In this way, it is assured that the cavity is always completely filled. Moreover, any air inside the cavity is expelled through the overflow area 13. Moreover, the overflow area 13 may be connected to a space 12 via one or several channels 11 as shown in FIG. 3. The cavity ends with a peripheral slit or groove 14, which is connected to the overflow area 13 over at least a portion. Thus, air inside the cavity is moved downward as seen in FIG. 1 to the groove 14 and further to the overflow area 13 and the space 12 via channel 11. Some material will be collected in the groove 14 and further in the overflow area 13. The material collected in the groove 14 may form an outer roll rib 55 on the urisheath, shown in FIG. 5. The roll rib may facilitate the handling of the urisheath after the production process. For the ready-made urisheath the roll rib gives good quality of the rolling, without wrinkles, and thus gives good unrolling for the user, and thereby secures a proper attachment on the user without having any wrinkles on the urisheath. This is essential for preventing a leakage. Furthermore, the roll rib may also increase the durability of the urisheath since the thin wall of the cylindrical portion 54 may have low tear strength and the roll rib may strengthen the distal end portion of cylindrical portion 54 of the urisheath. The material, which is collected in the overflow area 13, may simply be removed after the curing of the urisheath, such as during removal of the urisheath from the core.

The overflow area 13 may extend over a portion of the periphery of the core or insert, such as over almost 180° as shown in FIG. 3, or over a smaller portion, such as 90°.

The space 12 may be sufficiently large to accommodate the air that needs to be expelled from the cavity, or may be connected to the atmosphere.

In some embodiments, the overflow area 13 may not be required, but the channel 11 and the space 12 may accommodate the surplus air.

The material may be a liquid silicone elastomer material, such as a liquid silicone rubber LSR or a solid silicone (HCR, high consistency rubber).

A silicone elastomer is used because it has a relatively high gas permeability compared to for example thermoplastics. Moreover, it includes no phthalates or other organic plasticizers that may be harmful for the user or the environment. The material is heat stable and may be autoclaved.

An example of such a material, which may be suitable for use in the present invention, is a silicone elastomer No. C6-530 marketed by Dow Corning Co. The material is a two-component, platinum-catalyzed liquid silicone rubber elastomer. The two components are mixed in equal proportions, which are thoroughly blended. The elastomer is thermally cured via an addition-cure, platinum-catalyzed reaction. The resulting elastomer consists of cross-linked dimethyl and methyl-vinyl siloxane copolymers and reinforcing silica. The elastomer can be used without any post-cure. The elastomers are heat stable up to 204° C. Airless mixing, metering and dispensing equipment are recommended for production operations. Cure of the mixed elastomer is accelerated by heat. This material has been shown to be particularly suitable for the purpose of the present invention.

The material is injected in a cold state by the coldrun nozzle 20. The temperature of the material before being injected is between 5° C. and 50° C., specifically between 15° C. and 40° C., more specifically between 20° C. and 30° C., still more specifically about 25° C.

The form plates surrounding the cavity are heated to a temperature of between 80° C. and 200° C., specifically between 100° C. and 160° C., more specifically between 110° C. and 150° C., still more specifically between 135° C. and 145° C.

The material is injected rapidly into the cavity under high pressure of more than 1000 Bar, such as between 1500 to 2200 Bar. At this pressure, the material is a slightly viscous flowing material that can be injected at room temperature.

Thus, the material fills the cavity in less than a second, such as less than a few tenths of a second. The material cures rapidly, in less than three seconds. The material is metered by a pump, not shown, so that a sufficient quantity is injected to fill the cavity. Alternatively, the injection can be time operated, so that injection takes place a sufficient time period to fill the cavity.

Figure 4:
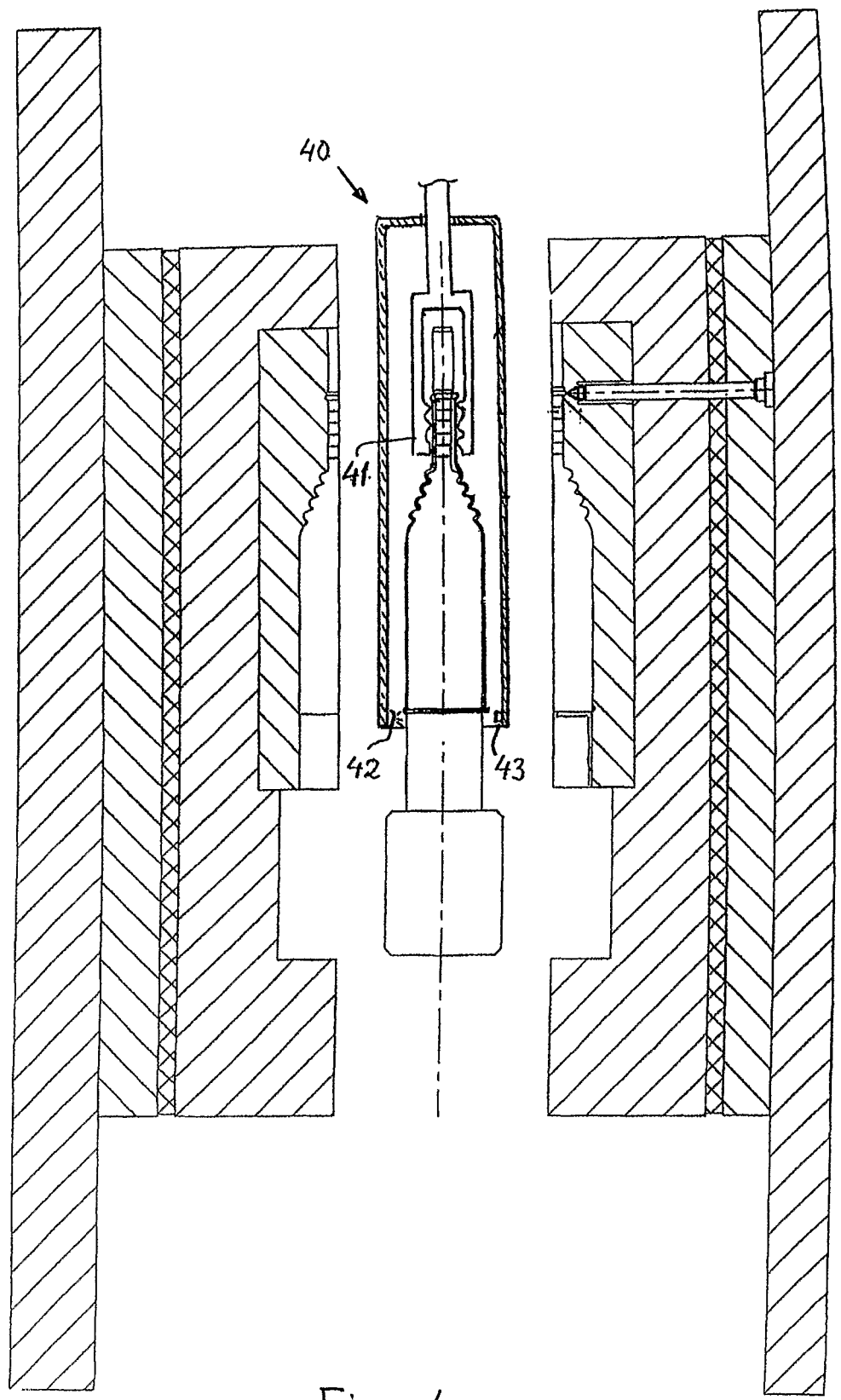
FIG. 4 is a cross-sectional view similar to FIG. 3 and shows a removing device.

When the material has cured in the cavity, the form is opened as shown in FIGS. 3 and 4. The injection-molded urisheath may be removed by grasping it at the enlarged tip portion 52 at the top of the core by a remover 40, as shown in FIG. 4. The remover 40 comprises a grip member 41 which may grasp the urisheath. The grip member comprises ridges, which interfere with small ribs arranged at the outer surface of the tip portion 52 of the urisheath. The grip member is arranged in a sleeve 42, which is moved down over the urisheath, when the form is opened. Moreover, air under pressure may be injected to make free the urisheath from the core and aid in the removal of the urisheath.

The remover pulls the urisheath from the core. Since the urisheath is elastic, it is no problem to withdraw it from the core, although the urisheath includes some portions that have to expand to pass the core, viz. pleated or folded portions in the middle part 53 connecting the tip portion 52 with the cylindrical portion 54 as shown in FIG. 5. Any material extending into the overflow area 13 may be cut off or torn off during the pulling out of the urisheath.

The cylindrical portion of the urisheath may be rolled before removing the urisheath from the core, which will make easier the removal of the urisheath from the core.

The remover includes an indication device 42, 43 for indicating that the entire urisheath has been removed and that no material is left in the cavity. This may be accomplished by sensors, such as LED:s and light sensors arranged to measure the entire length of the urisheath after removal from the core. If the urisheath has the expected length over the entire periphery, it is an indication that no material has been left in the cavity.

The urisheath may be exposed to further treatments after the production, either immediately, or at another site. Such later treatment may be the addition of an adhesive material and rolling the cylindrical portion.

Any material left in the overflow area 13 is removed, for example by introducing airflow into the area 13 and the channel/s 11. Thus, the removal of such material is ensured. This ensures that any material left from the previous injection molding operation, do not interfere with the closing operation of the form plates and cavity. Then, the cavity is closed in the opposite order for the next cycle. The injection machine has several guides for controlling the movement of the form portions so that no jamming may occur. The mold portions are manufactured with a very high precision so that no or negligible burrs occur in the areas of intersection between the form portions. Moreover, any residual material in the injection area should be as small as possible. Thus, the injection opening is made as small as possible, only some hundred micrometers.

Because of the shape of the cavity, the material fills the cavity in a smooth and equal manner, so that the cavity may be completely filled before any substantial curing has taken place. The material thickness in the cylindrical portion may be from 0.1 to 0.5 mm, such as 0.15 to 0.30 mm, for example, 0.25 mm.

The inner surfaces of the form sections 2, 3 delimiting the cavity may be surface treated in order to provide a certain roughness of the product. Thus, the surface may be grit blasted to level out any sharp surface irregularities, for preventing that the surface of the product will be damaged when the product is removed. Moreover, any pores in the cavity surface are closed.

Grit blasting is a mold finishing process in which abrasive particles are blasted onto the mold surfaces in order to produce a roughened surface. The grit may consist of iron, aluminum oxide or any crushed or irregular abrasive.

The blasted surface of the cavity will also provide a certain roughness of the surface of the ready-made product, which will prevent the product from adhering to it or to other products when they are stored or packed.

The insertion plates 9 may be exchanged if a urisheath with another dimension should be manufactured.

In order to remove the urisheath from the core, the core can be rotated 180° from the position shown in FIG. 4, so that the tip portion faces downward. For this purpose, pivoting axes may be arranged.

The entire procedure of injection molding the urisheath may take only about 30 to 40 seconds, which is the cycle time. If two or up to eight cores are arranged in parallel in the machine, a high capacity may be obtained. No post-curing is normally required. However, post-curing may be used for some types of material.

Above, the production of a urisheath has been described. The same procedure may be used for producing other types of thin-walled products, such as a balloon or any hollow product having at least one opening. One such exemplifying product is a gastrobelt, which is a type of balloon for strangling the stomach.

Herein above has been described an injection molding method and machine for producing a product, such as a urisheath. However, the invention is not limited to the embodiments disclosed. The different steps can be performed in other combinations than those identified above. Other means normally used within the field of the invention may replace those defined above. The invention is only limited by the appended patent claims.

The invention claimed is:

1. A method of producing a hollow urisheath product in an injection molding machine, including a mold comprising an annular cavity defined by a core and at least one side portion, where said cavity has an inlet and a narrow cross-sectional area over a substantial portion of said cavity and said cavity is connected to a venting area; the method comprising: injecting a silicone material into said inlet of said cavity; curing by heating said injected material in said cavity, said heating comprising heating said core to a temperature of between about 100° C. and about 160° C.; opening said mold by moving said at least one side portion to expose said core with the cured material forming said product; and removing said product from said core by grasping one end adjacent said inlet and pulling said product from said core, wherein said cavity has an annular enlarged portion at the proximal portion of said cavity, arranged adjacent said inlet, and wherein said urisheath product is produced.

2. The method according to claim 1, wherein said cavity further comprises a groove at the distal portion of said cavity.

3. The method according to claim 1, wherein said narrow cross-sectional area has a decreasing radial dimension towards the distal portion of said cavity.

4. The method according to claim 1, wherein said cavity is blasted.

5. The method according to claim 1, wherein said mold comprises said annular cavity defined by said core and two side portions.

6. The method according to claim 1, further comprising: injecting said silicone material into said cavity by a coldrun nozzle in a cold state.

7. The method according to claim 1, further comprising: injecting said material into said cavity until material is received in said venting area.

8. The method according to claim 1, wherein said material is a liquid silicone elastomer material or a solid silicone material.

9. The method according to claim 1, wherein said core is heated between a temperature of about 100° C. and about 150° C.

10. The method according to claim 1, wherein said core is heated between a temperature of about 110° C. and about 160° C.

11. A method of producing a hollow urisheath product in an injection molding machine, including a mold comprising an annular cavity defined by a core and at least one side portion, where said cavity has an inlet, a groove at a distal portion of said cavity and a narrow cross-sectional area over a substantial portion of said cavity and said cavity is connected to a venting area; the method comprising: injecting a silicone material into said inlet of said cavity; curing by heating said injected material in said cavity, said heating comprising heating said core to a temperature of between about 100° C. and about 160° C.; opening said mold by moving said at least one side portion to expose said core with the cured material forming said product; and removing said product from said core by grasping one end adjacent said inlet and pulling said product from said core, wherein said urisheath product is produced.

12. The method according to claim 11, wherein said core is heated between a temperature of about 100° C. and about 150° C.

13. A method of producing a hollow urisheath product in an injection molding machine, including a mold comprising an annular cavity defined by a core and at least one side portion, where said cavity has an inlet and a narrow cross-sectional area over a substantial portion of said cavity and said cavity is connected to a venting area; the method comprising: injecting a silicone material into the inlet of said cavity; curing by heating said injected material in said cavity, said heating comprising heating said core to a temperature of between about 100° C. and about 160° C.; opening said mold by moving said at least one side portion to expose said core with the cured material forming said product; and removing said product from said core by grasping one end adjacent said inlet and pulling said product from said core, wherein said narrow cross-sectional area has a decreasing radial dimension towards the distal portion of said cavity, and wherein said urisheath product is produced.

14. The method according to claim 13, wherein said core is heated between a temperature of about 100° C. and about 150° C.

15. The method according to claim 13, wherein said core is heated between a temperature of about 110° C. and about 160° C.

16. A method of producing a hollow urisheath product in an injection molding machine, including a mold comprising an annular cavity defined by a core having an inlet and at least one side portion, where said cavity has a narrow cross-sectional area over a substantial portion of said cavity and said cavity is connected to a venting area; the method comprising: injecting a silicone material into said inlet of said cavity; curing by heating said injected material in said cavity, said heating comprising heating said core to a temperature of between about 100° C. and about 160° C.; opening said mold by moving said at least one side portion to expose said core with the cured material forming said product; and removing said product from said core by grasping one end adjacent said inlet and pulling said product from said core, wherein said cavity is grit blasted, and wherein said urisheath product is produced.

17. The method according to claim 16, wherein said core is heated between a temperature of about 100° C. and about 150° C.

18. The method according to claim 16, wherein said core is heated between a temperature of about 110° C. and about 160° C.

* * * * *